United States Patent

Volpicelli et al.

(10) Patent No.: US 8,084,629 B2
(45) Date of Patent: Dec. 27, 2011

(54) PROCESS FOR PREPARING NEBIVOLOL

(75) Inventors: Raffaella Volpicelli, Vicenza (IT); Paolo Maragni, Virgilio (IT); Franco Massaccesi, Grancona (IT); Ilaria Munari, Vicenza (IT); Livius Cotarca, Cervignano del Friuli (IT); Johnny Foletto, Arcole (IT)

(73) Assignee: Zach System S.p.A., Bresso (MI) (IT)

( * ) Notice: Subject to any disclaimer, the term of this patent is extended or adjusted under 35 U.S.C. 154(b) by 0 days.

(21) Appl. No.: 12/935,150

(22) PCT Filed: Mar. 16, 2009

(86) PCT No.: PCT/EP2009/053051
§ 371 (c)(1),
(2), (4) Date: Sep. 28, 2010

(87) PCT Pub. No.: WO2009/121710
PCT Pub. Date: Oct. 8, 2009

(65) Prior Publication Data
US 2011/0021793 A1    Jan. 27, 2011

(30) Foreign Application Priority Data

Mar. 31, 2008  (IT) .............................. MI2008A0547

(51) Int. Cl.
*C07D 407/04* (2006.01)
*C07D 311/14* (2006.01)
(52) U.S. Cl. ...................................................... 549/407
(58) Field of Classification Search .................. 549/407
See application file for complete search history.

(56) References Cited

FOREIGN PATENT DOCUMENTS

EP     1 803 715     7/2007
WO     2008/064826  6/2008

OTHER PUBLICATIONS

Ramachandran, P.V. et al., "Efficient general synthesis of 1,2- and 1,3-diols in high enantiomeric excess via the intramolecular asymmetric reduction of the corresponding ketoalkyl diisopinocampheylborinate intermediates" Tetrahedron Letters, vol. 38., No. 5, 1997, pp. 761-764.
Srebnik, M. et al., "Chiral synthesis via organoboranes. 18. Selective reductions. 43. Diisopinocampheylchloroborane as an excellent chiral reducing reagent for the synthesis of halo alcohols of high enantiomeric purity. A highly enantioselective synthesis of both optical isomers of Tomoxetine, Fluoxetine, and Nisoxetine" J. Org. Chem., vol. 53., No. 13, 1988, pp. 2916-2920.
Cho, B.T. et al., "Facile Synthesis of Optically Active Styrene Oxide Derivatives by Asymmetric Reduction of Substituted 2-Sulfonyloxyacetophenomes with (−)-B-Chlorodiisopinocampheylborane" Bulletin of the Korean Chemical Society, vol. 22., No. 5, 2001, pp. 443-444.

*Primary Examiner* — Bernard Dentz
(74) *Attorney, Agent, or Firm* — Lucas & Mercanti, LLP

(57) ABSTRACT

The present invention relates to a process for reducing a compound of formula (I) wherein X is halogen, a hydroxy group, an alkylsulfoniloxy group or an arylsulfonyloxy group; to give a compound of formula (II) as a diastereoisomerically pure compound of RS/SR configuration characterized in that said reduction is carried out by the use of (+)-B-chlorodiisopinocampheylborane or (−)-B-chlorodiisopinocampheylborane. The compounds of formula (II) are useful as intermediates for the preparation of Nebivolol.

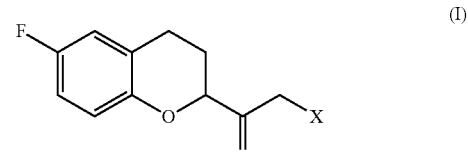

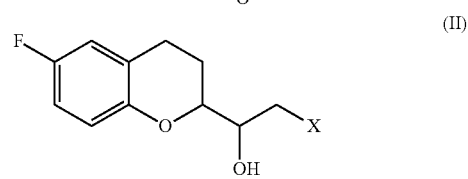

14 Claims, No Drawings

PROCESS FOR PREPARING NEBIVOLOL

This application is a U.S. national stage of PCT/EP2009/053051 filed on Mar. 16, 2009 which claims priority to and the benefit of Italian Application No. MI2008A000547 filed on Mar. 31, 2008, the contents of which are incorporated herein by reference.

The present invention relates to a process for preparing Nebivolol and, more particularly, to a method for stereoselective reduction of an alpha-haloketone of formula

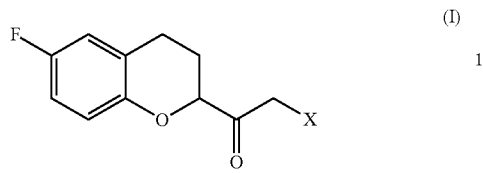

intermediate useful for the preparation of nebivolol.

Nebivolol (hereafter, NBV), is a mixture of equal amounts of [2S[2R*[R[R*]]]]α,α'-[imino-bis(methylene)]bis[6-fluoro-chroman-2-methanol] (hereafter d-NBV) of formula (IA)

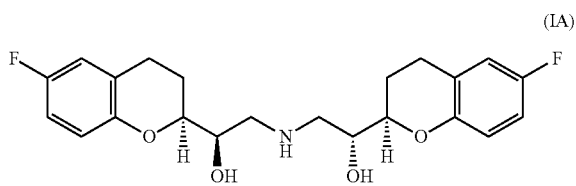

and its [2R [2S*[S[S*]]]]enantiomer (hereafter /-NBV) of formula (IB)

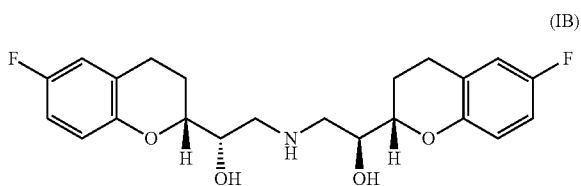

Nebivolol is characterized by its adrenergic β-blocking properties and is useful in treating essential hypertension. It has basic properties and may be converted into its addition salts through treatment with suitable acids. The hydrochloric acid addition salt is the marketed product.

It is known in the art that the synthesis of α,α'-[imino-bis(methylene)]bis[chroman-2-methanol] molecular structures is challenging for the skilled person because of the four asymmetric carbon atoms producing a mixture of 16 stereoisomers (in case of asymmetrical substitutions) or a mixture of 10 stereoisomers (in case of symmetrical substitutions). As apparent from the presence of symmetry in the nebivolol structure, a total of 10 stereoisomers may be generated.

Literature reports several processes for the preparation of nebivolol.

The patent EP 145067 (Janssen Pharmaceutica NV) describes a method of preparing NBV which comprises synthesizing diastereoisomeric mixtures of chroman epoxide derivatives in accordance with the synthetic scheme below

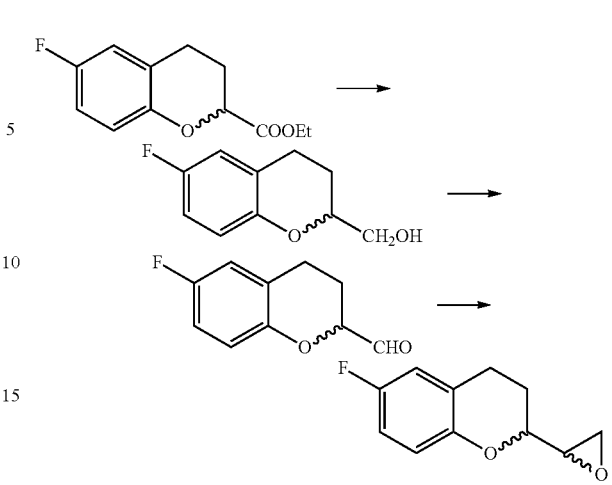

The 6-fluoro chroman carboxylic acid ethyl ester, derived from the esterification of the corresponding acid, is reduced with sodium dihydro bis-(2-methoxyethoxy)-aluminate to primary alcohol; the product is reacted with oxalyl chloride and then triethylamine at −60° C. to give the corresponding racemic aldehyde, which is then converted into epoxide as a mixture of (R,S), (S,R), (R,R) and (S,S) stereoisomers, which in turn are separate chromatographically in two racemic mixtures (R,S)-, (S,R)-epoxide (Mixture A) and (S,S)-, (R,R)-epoxides (Mixture B), respectively. Said epoxide derivatives represent the key intermediates of the process.

The patent EP 334429 (Janssen Pharmaceutica NV) describes substantially the same synthetic process reported in the previous patent and is particularly directed to the preparation of single optical isomers (R,S,S,S) and (S,R,R,R) of NBV.

In this instance, the 6-fluoro chroman carboxylic acid is resolved into single enantiomers by treatment with (+)-dehydroabiethylamine. Said single enantiomers are separately converted into their corresponding epoxides resulting in a mixture of two diastereoisomers. The following synthetic scheme describes, for example, the conversion of the S-acid derivative.

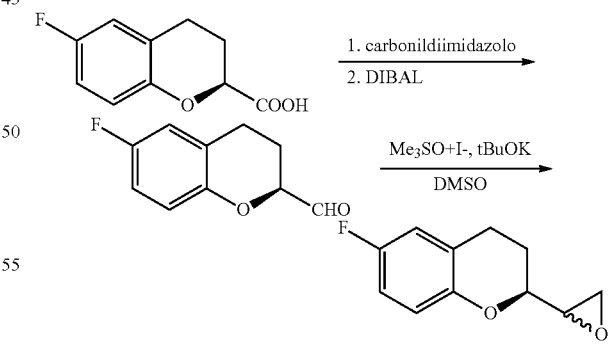

The co-pending patent application PCT/EP2007/008549 in the name of the same Applicant describes an improved method for the synthesis of 6-fluoro chroman epoxides that comprises the conversion of an alkyl or aryl 6-fluoro-3,4-dihydro-2H-chromen-2-carboxylate in 2-halo-1-(6-fluoro-3,4-dihydro-2H-chromen-2-yl)ethanone (hereafter, alpha-haloketone) via sulfoxonium ylide; the reduction of said alpha-haloketone to yield the corresponding 2-halo-1-(6-fluoro-3, 4-dihydro-2H-cromen-2-yl)-ethanol (hereafter halohydrin); and the cyclization in the presence of a base to yield the corresponding epoxide derivative as a mixture of four stereoisomers (R,S), (S,R), (R,R) and (S,S), respectively.

The reduction reaction is carried out according to known techniques.

Specifically, said reduction of the alpha-haloketone intermediate takes place by means of sodium borohydride in the presence of an alcoholic solvent, among which ethanol, optionally in an aqueous mixture, is preferred.

The patent applications EP1803715 and EP1803716 (Cimex Pharma AG and University of Zurich) describe an alternative process for the preparation of NBV in racemic form and of its pure enantiomers.

The process foresees, inter alia, to provide a compound of formula

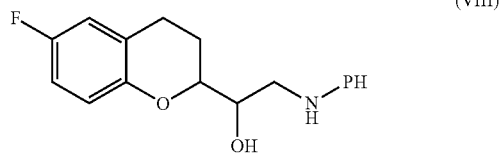

(VIII)

as a diastereoisomerically pure compound comprising at least 95% of RS/SR or RR/SS configuration wherein PG is hydrogen or an amine protecting group. Said providing a compound of formula VIII includes the preparation of a racemic compound of formula

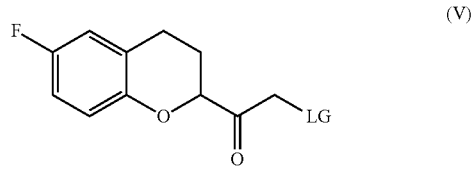

(V)

wherein
LG is a chlorine or bromine atom; the reduction of a racemic compound of formula V in a solvent and, optionally, in the presence of a Lewis acid to give a diastereoisomeric mixture of a compound of formula

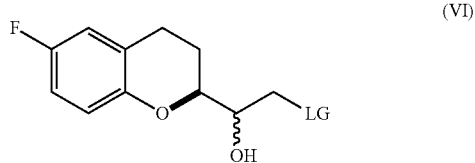

(VI)

forming a mixture of diastereoisomers of a compound of formula

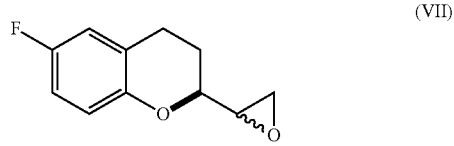

(VII)

reacting the diastereoisomers of the compound of formula VII with $NH_2PG$ to give a compound of formula VIII as a mixture of diastereoisomers and optically separating the diastereoisomers of the compound of formula VIII from the mixture of diastereoisomers through fractioned crystallization, optionally after formation of a salt.

Within said process, several methods are described for reducing the intermediate of formula V to give a compound of formula VI in two possible racemic mixture having sin(RR/SS) or anti (RS/SR) configuration.

In particular, a series of reducing agents, catalysts, solvents and reaction conditions were tested (see EP1803715 Table 2, pages 33-37) with the aim of obtaining racemic mixtures useful for the preparation of NBV.

However, the reduction attempts performed had as a result the obtainment of racemic mixtures having variable ratios of the RR/SS over RS/SR configurations.

Given the lack of success of the hypothesis of a diastereoselective reduction that leads to high diastereoisomeric excesses able to avoid a chromatographic separation, the patent application provides for the mixture of the compounds of formula VI to be converted via chroman epoxide VII into a compound of formula VIII whose fractioned crystallization would allow to obtain mixtures of stereoisomers useful for the continuation of the synthesis.

Of note is the presence after crystallization of an amount of around 5% of the undesired pair of stereoisomers.

It is known in the art the essential role of the 6-fluoro-chroman epoxide compound in preparing NBV.

In light of the specific stereochemistry of the active ingredient, the role of said epoxide in the form of a useful racemic mixture or of the related single stereoisomers is even more critical.

Therefore, it would be desirable to study alternative methods for preparing the intermediate, which allow to overcome the drawbacks presented by the processes described by the prior art.

We have now, surprisingly, found a simple and efficient synthesis of 6-fluoro-chroman epoxides in the form of racemic mixtures useful for the preparation of NBV, via stereoselective reduction of known alpha-haloketones derivatives through the use of (+)- or (−)-B-chlorodiisopinocampheylborane as a reducing agent. Therefore, it is a first object of the present invention a process for reducing a compound of formula

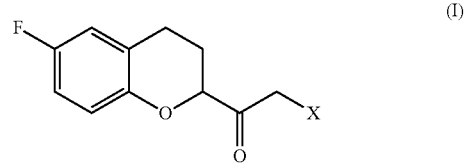

(I)

wherein X is halogen, a hydroxy group, an alkylsulfoniloxy group or an arylsulfonyloxy group;

to give a compound of formula

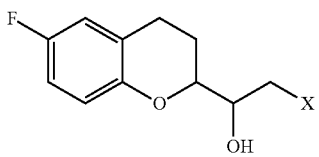

(II)

as a diastereoisomerically pure compound of RS/SR configuration characterized in that said reduction is carried out by the use of (+)-B-chlorodiisopinocampheylborane or (−)-B-chlorodiisopinocampheylborane.

The compound of formula I can be prepared according to known techniques, in particular, according to the processes described in the co-pending patent application PCT/EP2007/008549 and applications EP1803715 and EP1803716.

(+)-B-chlorodiisopinocampheylborane, commonly identified as (+)-DIP-Chloride™, is a known reducing agent commercially available in solid form.

(−)-B-chlorodiisopinocampheylborane, commonly identified as (−)-DIP-Chloride™, also is a known reducing agent commercially available in solid form or in solution. The reduction of ketone groups by reducing agents such as organoboranes and, in particular, through the use of the specific reducing agents object of the invention is known in the art.

Generally, the reaction of a compound of formula I with (+)- or (−)-DIP-Chloride™ to give a compound of formula II is carried out in the presence of one or more organic solvents, optionally in admixture.

The reduction object of the invention can also be carried out en masse.

Solvents suitable for the reduction object of the invention are inert organic solvents like hydrocarbons such as benzene, xylene, toluene, hexane, cyclohexane, heptane, octane and the like; chlorinated hydrocarbons such as methylene chloride, ethylene dichloride, carbon tetrachloride and the like; nitryls such as acetonitryl, benzonitryl and the like; aprotic dipolar solvents such as dimethyl sulfoxide, dimethylformamide and the like; cyclic ethers such as dioxane, tetrahydrofuran and the like; linear ethers such as ethyl ether, methyl-tert-butyl ether and the like; or mixtures thereof.

Preferred solvents are methyl-tert-butyl-ether, tetrahydrofuran, heptane, hexane, toluene or mixtures thereof.

Among the solvents, still more preferred is toluene.

Generally, the reaction of a compound of formula I with (+)- or (−)-DIP-Chloride™ to give a compound of formula II is carried out at a temperature between −78° C. and 100° C.

Preferably, the reduction is carried out at a temperature between −25° C. and 25° C. Still more preferably, the reduction is carried out at a temperature around 0° C.

In one aspect of the invention, the mixture obtained by reaction of a compound of formula I with a reducing agent object of the invention can be neutralized, according to conventional techniques, through the addition of a derivative able to complex boranate by-products.

In general, ethanolamine is used to eliminate via filtration the diethanolamine-boron crystalline complex.

Generally, in the reduction object of the invention molar ratios equal to or greater than 1 between reducing agent and substrate are used.

Preferably the reduction reaction object of the present invention is carried out by the use of (+)-B-chlorodiisopinocampheylborane.

In one aspect of the invention, the reaction is carried out by adding a solution of a compound of formula I in a suitable solvent to a solution of the reducing agent, preferably (+)-B-chlorodiisopinocampheylborane, in a suitable solvent maintained at a temperature between −78° C. and 100° C.

In a preferred aspect of the invention, a compound of formula I is added to the reducing agent at a temperature between −25° C. and 25° C.

Preferably, a compound of formula I is added to the reducing agent at a temperature around 0° C.

It is another object of the present invention a process for preparing a compound of formula

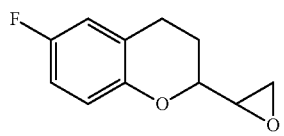

(III)

as a diastereoisomerically pure compound of RR/SS configuration which comprises a reduction process as set out above.

It is another object of the present invention a process for preparing a compound of formula

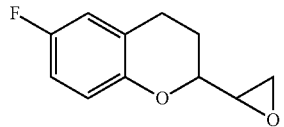

(III)

as set out above which further comprises the reaction of a compound of formula II with a base to give an epoxide compound of formula III.

The reaction of a compound of formula II to give a compound of formula III is carried out according to known techniques.

In one aspect of the invention the cyclization of a compound of formula II to give the epoxide compound of formula III is carried out as set out in the aforesaid co-pending patent application PCT/EP2007/008549.

In general, cyclization is carried out through a reaction of a compound of formula II with alcoxides or alkaline hydroxides in the presence of alcoholic solvents or ethers, optionally in admixture.

According to a preferred aspect of the invention, the reaction is carried out with a base such as potassium t-butoxide in the presence of an isopropanol/THF mixture. Alternatively, the reaction is carried out with a base such as sodium hydroxide in the presence of isopropanol.

The temperature of the reaction is generally between −25° C. and 100° C.

Preferably, the cyclization reaction is carried out at a temperature around 0° C.

In the present invention the term halogen means an atom of fluorine, chlorine, bromine and iodine.

Suitable outgoing groups such as alkyl or aryl sulfonates are known to the skilled person.

Preferably X is halogen, a hydroxy group or an appropriate outgoing group such as mesylate or tosylate.

Still more preferably X is a hydroxy group.

Still more preferably X is a chlorine atom.

In the present invention, the expression to give a compound of formula II as diastereoisomerically pure compound of RS/SR configuration means a compound obtained as a substantially pure mixture of the optical isomers of RS and SR configuration i.e. of the enantiomers (S)-2-chloro-1-((R)-6-fluoro-3,4-dihydro-2H-chromen-2-yl)-ethanol and (R)-2-chloro-1-((S)-6-fluoro-3,4-dihydro-2H-chromen-2-yl)-ethanol.

In the present invention, the expression to give a compound of formula III as diastereoisomerically pure compound of RR/SS configuration means a compound obtained as a substantially pure mixture of the optical isomers of RR and SS configuration i.e. of the enantiomers (R)-6-fluoro-3,4-dihydro((R)-oxiran-2-yl)-2H-chromen and (S)-6-fluoro-3,4-dihydro((S)-oxiran-2il)-2H-chromen.

For the purposes of the present invention, it is readily apparent that it is preferable to obtain a racemic mixture of the compounds of formula II and/or III defined above which, appropriately treated, lead to the preparation of the NBV end product.

Said partially resolved epoxide derivatives represent, as it is well known, key intermediates in the NBV preparation process.

It is another object of the present invention a process for synthesizing nebivolol which comprises the reduction of a compound of formula

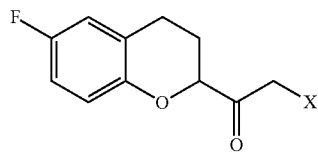

(I)

wherein X is defined above;
to give a compound of formula

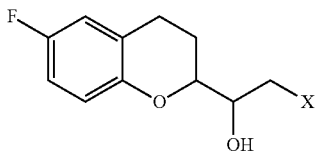

(II)

as a diastereoisomerically pure compound of RR/SS configuration as set out above. The process object of the present invention comprises the use of a reagent that is readily available on the market.

DIP-Chloride™ is a well known chiral reagent which is, however, commonly used in asymmetrical, enantioselective reductions of prochiral ketonic substrates.

Therefore, first of all, it is worth noting that, surprisingly, in the reduction reaction according to the invention both (+)- and (−)-Dip-Chloride™ were revealed to be excellent diastereoselective reducing agents able to provide a product characterized by high diastereoisomeric excesses (RS/SR around 99% de at the halohydrin level and RR/SS around 98% de following chroman epoxide cyclization) and, additionally, by low enantiomeric excesses.

Moreover, the most relevant inventive aspect that can be associated to the process of the invention is without any doubt the possibility to avoid the chromatographic separation of the intermediates with an optical configuration useful to the process for preparing the racemic mixture of NBV.

Hence, it is readily apparent that the reduction method object of the invention constitutes an efficient and economical synthetic alternative in the preparation of key intermediates in the preparation of the active ingredient NBV.

Another object of the present invention are the compounds:
(S*)-2-chloro-1-((R*)-6-fluoro-3,4-dihydro-2H-chromen-2-yl)-ethanol characterized by a diastereoisomeric excess of at least 99%; and
(R*)-6-fluoro-3,4-dihydro((R*)-oxiran-2-yl)-2H-chromen characterized by a diastereoisomeric excess of at least 98%;
as useful intermediates in the preparation of nebivolol.

It is another object of the present invention a process for reducing a compound of formula I as set out above, characterized in that the compound of formula II, (S*)-2-chloro-1-((R*)-6-fluoro-3,4-dihydro-2H-chromen-2-yl)-ethanol, is obtained with a diastereoisomeric excess of at least 99%.

It is a further object of the present invention a process for the preparation of a compound of formula III as set out above characterized in that said compound of formula III, (R*)-6-fluoro-3,4-dihydro-2-((R*)-oxiran-2-yl)-2H-chromen, is obtained with a diastereoisomeric excess of at least 98%.

Still another object of the present invention is the use of (+)- or (−)-DIP-Chloride™ in the preparation of NBV.

A practical embodiment of the process object of the present invention comprises the reduction of a racemic alpha-haloketone of formula I to halohydrin of formula II by the use of (+)- or (−)-Dip-Chloride™ and the cyclization to epoxide derivative of formula III in the presence of a base.

A preferred practical embodiment of the process object of the present invention comprises the reduction of a racemic alpha-chloroketone of formula I to chlorohydrine of formula II by reaction with (+)-Dip-Chloride™ in the presence of an organic solvent, preferably an aromatic hydrocarbon, at a temperature comprised between −25° C. and 25° C., preferably around 0° C., and the cyclization to epoxide derivative of formula III by reaction with alcoxides or alkaline hydroxides in the presence of alcoholic solvents or ethers, optionally in admixture.

To better illustrate the invention the following examples are now given.

EXAMPLE 1

Synthesis of (S*)-2-chloro-14-(R*)-6-fluoro-3,4-dihydro-2H-chromen-2-yl)-ethanol A solution of (+)-B-chlorodiisopinocampheylborane [(+)-DIP-Chloride™] (2.10 g, 6.55 mmoles) in toluene (7 ml) is cooled to 0° C. under nitrogen atmosphere. On the magnetically stirred solution is added in 3 hours a solution of 2-chloro-1-(6-fluoro-3,4-dihydro-2H-chromen-2-yl)ethanone (1.0 g, 4.373 mmoles) in toluene (3 ml). At the end of the addition, the mixture is stirred at 0° C. for further 20 hours. On the reaction mixture is added acetone (0.5 g), followed by a 10% w/w (5 ml) aqueous solution of sodium carbonate, and then demi water (5 ml). The reactive mixture is heated to 20° C. at the end of the additions and transferred in a separator funnel. The mixture is diluted with demi water (5 ml) and toluene (5 ml) and phases are separated. The organic layer is then washed with additional demi water (15 ml) and concentrated and anhydrified under vacuum to obtain crude (S*)-2-chloro-1-((R*)-6-fluoro-3,4-dihydro-2H-chromen-2-yl)-ethanol (99% de via GC). The product is purified by chromatography on silica using a toluene:ethyl acetate 9:1 eluting mixture. After separation, the product (S*)-2-chloro- 1-((R*)-6-fluoro-3,4-dihydro-2H-chromen-2-yl)-ethanol is isolated as a colorless oil (0.64 g, 63%).

Diast. (SR,RS): δH (400 MHz; CDCl3) 6.83-6.73 (3H, m), 4.21-4.16 (1H, m), 3.94-3.88 (1H, m), 3.83-3.77 (1H, m), 3.74-3.68 (1H, m), 2.97-2.75 (2H, m), 2.45-2.33 (1H, —OH, b), 2.02-1.96 (2H, m);

m/z (EI) 230.050989 (M+. C11H12ClFO2 requires 230.05067).

EXAMPLE 2

Synthesis of (S*)-2-chloro-14-(R*)-6-fluoro-3,4-dihydro-2H-chromen-2-yl)-ethanol A solution of (−)-B-chlorodiisopinocampheylborane [(−)-DIP-Chloride™] (2.10 g, 6.55 mmoles) in toluene (7 ml) is cooled to 0° C. under nitrogen atmosphere. On the magnetically stirred solution is added in 3 hours a solution of 2-chloro-1-(6-fluoro-3,4-dihydro-2H-chromen-2-yl)ethanone (1.0 g, 4.373 mmoles) in toluene (3 ml). At the end of the addition, the mixture is stirred at 0° C. for further 20 hours. On the reaction mixture is added acetone (0.5 g), followed by a 10% w/w (5 ml) aqueous solution of sodium carbonate, and then demi water (5 ml). The reactive mixture is heated to 20° C. at the end of the additions and transferred in a separator funnel. The mixture is diluted with demi water (5 ml) and toluene (5 ml) and phases are separated. The organic layer is then washed with additional demi water (15 ml) and concentrated and anhydrified under vacuum to obtain crude (S*)-2-chloro-1-((R*)-6-fluoro-3,4-dihydro-2H-chromen-2-yl)-ethanol (98% de via GC). The product is purified by chromatography on silica using a toluene:ethyl acetate 9.5:0.5 eluting mixture. After separation, the product (S*)-2-chloro-1-((R*)-6-fluoro-3,4-dihydro-2H-chromen-2-yl)-ethanol is isolated as a colorless oil (0.31 g, 31%).

Diast. (SR,RS): δH (400 MHz; CDCl3) 6.83-6.73 (3H, m), 4.21-4.16 (1H, m), 3.94-3.88 (1H, m), 3.83-3.77 (1H, m), 3.74-3.68 (1H, m), 2.97-2.75 (2H, m), 2.45-2.33 (1H, —OH, b), 2.02-1.96 (2H, m);

m/z (EI) 230.050989 (M+. C11H12ClFO2 requires 230.05067).

EXAMPLE 3

Synthesis of (R*)-6-fluoro-3,4-dihydro-2-((R*)-oxiran-2-yl)-2H-chromen

The compound (S*)-2-chloro-1-((R*)-6-fluoro-3,4-dihydro-2H-chromen-2-yl)-ethanol obtained in Example 1 (320 mg, 1.387 mmoles) is dissolved in i-PrOH (2 ml) under nitrogen and the reaction mixture is cooled to 0° C. On the magnetically stirred mixture is added a 2M aqueous solution of sodium hydroxide (1.39 ml) in 10 min. The mixture is stirred for 2 hours at 0° C., then diluted with toluene (5 ml) and transferred in a separator funnel. The biphasic mixture is further diluted with toluene (5 ml) and demi water (5 ml) and the phases are separated. The organic phase is washed with demi water (10 ml) and concentrated under vacuum to yield (R*)-6-fluoro-3,4-dihydro((R*)-oxiran-2-yl)-2H-chromen as yellow oil (200 mg, 74%, 98% de via GC).

Diast. (RR,SS): δH (400 MHz; CDCl3) 6.81-6.72 (3H, m), 3.88-3.82 (1H, m), 3.21-3.17 (1H, m), 2.89-2.76 (4H, m), 2.1-2.00 (1H, m), 1.97-1.87 (1H, m).

EXAMPLE 4

Synthesis of (R*)-6-fluoro-3,4-dihydro-2-((R*)-oxiran-2-yl)-2H-chromen

The compound (S*)-2-chloro-1-((R*)-6-fluoro-3,4-dihydro-2H-chromen-2-yl)-ethanol obtained in Example 2 (200 mg, 0.867 mmoles) is dissolved in i-PrOH (1.6 g) under nitrogen and the reaction mixture is cooled to 0° C. On the magnetically stirred mixture is added a 2M aqueous solution of sodium hydroxide (0.9 ml) in 10 min. The mixture is stirred for 1 hour at 0° C., then diluted with toluene (5 ml) and transferred in a separator funnel. The biphasic mixture is further diluted with toluene (5 ml) and demi water (5 ml) and the phases are separated. The organic phase is washed with demi water (10 ml) and concentrated under vacuum to yield (R*)-6-fluoro-3,4-dihydro((R*)-oxiran-2-yl)-2H-chromen as yellow oil (110 mg, 87%, 95% de via GC).

Diast. (RR,SS): δH (400 MHz; CDCl3) 6.81-6.72 (3H, m), 3.88-3.82 (1H, m), 3.21-3.17 (1H, m), 2.89-2.76 (4H, m), 2.1-2.00 (1H, m), 1.97-1.87 (1H, m).

The invention claimed is:

1. A process for obtaining a compound of formula II

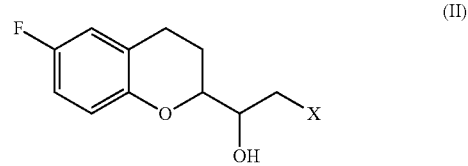

said process comprising
reducing a compound of formula I

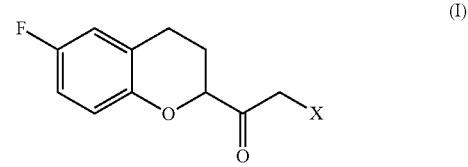

wherein X is halogen, a hydroxy group, an alkylsulfonyloxy group or an arylsulfonyloxy group; and
obtaining a compound of formula

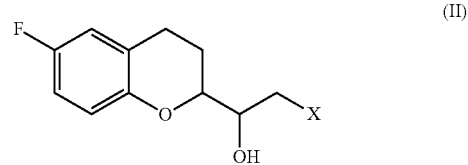

as a diastereoisomerically pure compound of RS/SR configuration wherein said reducing step is carried out with (+)-B-chlorodiisopinocampheylborane or (−)-B-chlorodiisopinocampheylborane.

2. A process according to claim 1 wherein said reducing step is carried out in the presence of one or more organic solvents.

3. A process according to claim 2 wherein said reducing step is carried out in toluene.

4. A process according to claim 1 wherein said reducing step is carried out at a temperature between −25° C. and 25° C.

5. A process according to claim 1 wherein said reducing step is carried out with a reducing agent/substrate molar ratio equal to or greater than 1.

6. A process for preparing a compound of formula

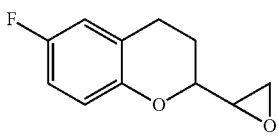
(III)

as a diastereoisomerically pure compound of RR/SS configuration, said method comprising a process according to claim 1.

7. A process according to claim 6 further comprising cyclizing a compound of formula II with a base, and obtaining a compound of formula III.

8. A process according to claim 7 wherein said cyclizing step is carried out by reacting a compound of formula II with alkoxides or alkaline hydroxides in the presence of alcoholic solvents or ethers.

9. A process for preparing nebivolol comprising a process according to claim 1.

10. A process according claim 1 wherein the reducing step is carried out with (+)-B-chlorodiisopinocampheylborane.

11. A process according to claim 1 wherein X is chlorine or a hydroxy group.

12. A compound of formula (S*)-2-chloro-14(R*)-6-fluoro-3,4-dihydro-2H-chromen-2-yl)-ethanol characterized by a diastereoisomeric excess of at least 99%.

13. A process according to claim 2, wherein said one or more organic solvents are in admixture.

14. A process according to claim 8, wherein said alcoholic solvents or ethers are in admixture.

* * * * *